(12) United States Patent
Pari et al.

(10) Patent No.: US 8,263,579 B2
(45) Date of Patent: Sep. 11, 2012

(54) ANTI-INFLAMMATORY COMPOUNDS

(75) Inventors: Koteppa Pari, Mumbai (IN); Girish Badrinath Mahajan, Mumbai (IN); Nidhi Tomar, Mumbai (IN); Vijaya Phani Kumar Yemparala, Mumbai (IN); Asha Adrian Kulkarni-Almeida, Mumbai (IN); Saji George, Mumbai (IN)

(73) Assignee: Piramal Healthcare Limited, Mumbai (IN)

( * ) Notice: Subject to any disclaimer, the term of this patent is extended or adjusted under 35 U.S.C. 154(b) by 0 days.

(21) Appl. No.: 13/012,463

(22) Filed: Jan. 24, 2011

(65) Prior Publication Data
US 2012/0190651 A1 Jul. 26, 2012

(51) Int. Cl.
*C07D 498/06* (2006.01)
*C07C 291/08* (2006.01)
*A61K 31/655* (2006.01)
*A61K 31/5365* (2006.01)
*A61P 29/00* (2006.01)

(52) U.S. Cl. ........ 514/150; 514/450; 534/556; 540/455; 560/316

(58) Field of Classification Search .................. None
See application file for complete search history.

(56) References Cited

U.S. PATENT DOCUMENTS
4,460,513 A * 7/1984 Mendenhall .................. 560/316

OTHER PUBLICATIONS

Tageja et al., "New Targets for the Treatment of Follicular Lymphoma", Journal of Hematology and Oncology, 2(50), 1-14, 2009.*

* cited by examiner

*Primary Examiner* — Fiona T Powers
(74) *Attorney, Agent, or Firm* — Ladas & Parry LLP

(57) ABSTRACT

This invention relates to novel compounds obtained by fermentation of Myxobacteria strain (PM0670013/MTCC 5570). The present invention further relates to the processes for the production of the novel anti-inflammatory compounds, to the culture no. PM0670013 (MTCC 5570), and to pharmaceutical compositions containing compounds of the present invention as an active ingredient and its use in medicines for the treatment of inflammatory diseases or disorders mediated by proinflammatory cytokines such as Tumor Necrosis Factor-alpha (TNF-α) and/or interleukins such as IL-6, having anti-inflammatory activity The invention also includes all stereoisomeric forms of compounds of the present invention.

8 Claims, 2 Drawing Sheets

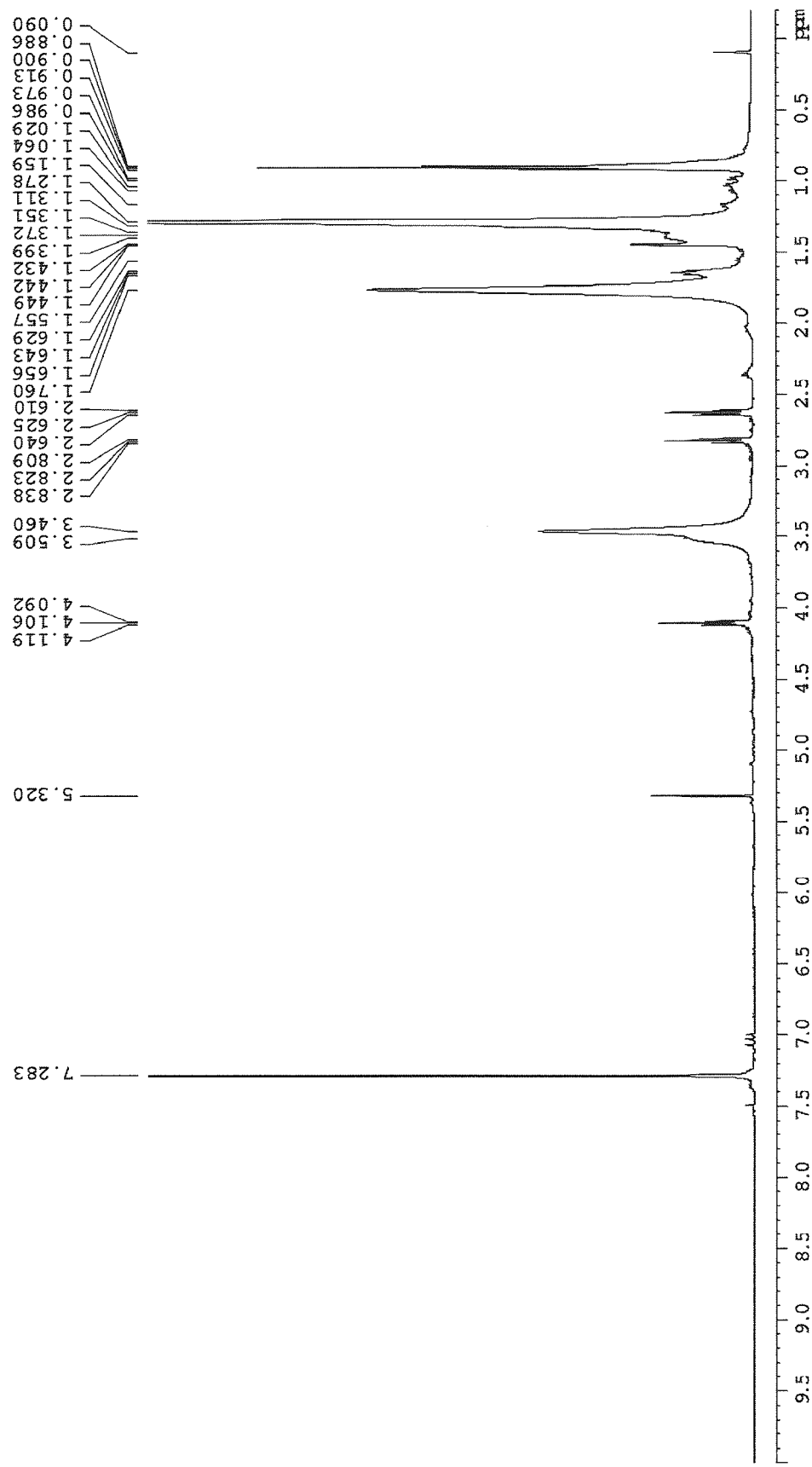
Figure 1: ¹H NMR spectrum of the compound of formula I

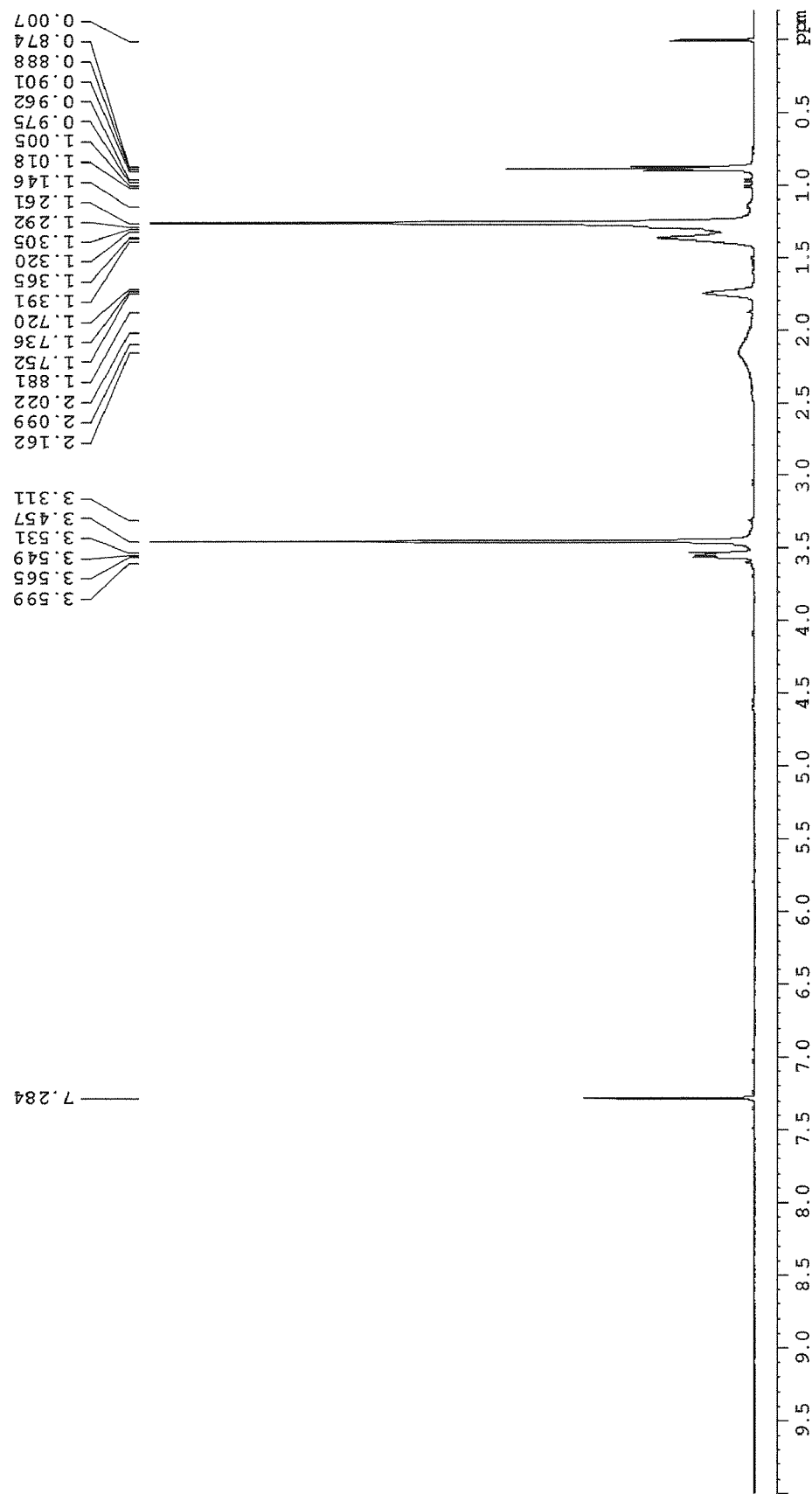
Figure 2: $^1$H NMR spectrum of the compound of formula II

ANTI-INFLAMMATORY COMPOUNDS

FIELD OF THE INVENTION

This invention relates to novel compounds obtained by fermentation of Myxobacteria strain (PM0670013/MTCC 5570). The present invention further relates to the processes for the production of the novel anti-inflammatory compounds, to the culture no. PM0670013 (MTCC 5570), and to pharmaceutical compositions containing one or more compounds of the present invention as an active ingredient and its use in medicines for the treatment of inflammatory diseases or disorders mediated by proinflammatory cytokines such as Tumor Necrosis Factor-alpha (TNF-α) and/or interleukins such as Interleukin-6 (IL-6). The invention also includes all stereoisomeric forms of compounds of the present invention.

BACKGROUND OF THE INVENTION

Proinflammatory cytokines, especially TNF-α and interleukins (IL-β, IL-6, IL-8) play an important role in the inflammatory process. They are produced by a variety of cell types, but most important sources are macrophages and monocytes at inflammatory sites. An increase in TNF-α synthesis/release is a common phenomenon during the inflammatory process. Inflammation is an inherent part of various disease states like rheumatoid arthritis, Crohn's disease, ulcerative colitis, septic shock syndrome, atherosclerosis, among other clinical conditions.

TNF-α has been implicated as a mediator in inflammatory bowel disease, inflammation, rheumatoid arthritis, juvenile rheumatoid arthritis, psoriatic arthritis, osteoarthritis, refractory rheumatoid arthritis, chronic non-rheumatoid arthritis, osteoporosis/bone resorption, septic shock, endotoxic shock, atherosclerosis, ischemia-reperfusion injury, coronary heart disease, vasculitis, amyloidosis, multiple sclerosis, sepsis, chronic recurrent uveitis, hepatitis C virus infection, malaria, ulcerative colitis, cachexia, plasmocytoma, endometriosis, Behcet's disease, Wegenrer's granulomatosis, autoimmune diseases such as Crohn's disease, psoriasis or ankylosing spondylitis, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, meningitis, skin delayed type hypersensitivity disorders, Alzheimer's disease, systemic lupus erythematosus and allergic asthma.

Interleukin-6 (IL-6) is a pleiotropic cytokine that regulates immunological reactions involved in host defence, inflammation, haematopoiesis, and oncogenesis (Blood, 1989, 74(1), 1-10). IL-6 has a wide range of biological activities. It is known to be a B-cell differentiation factor, induces T cell growth and cytotoxic T-cell differentiation through effecting IL-2 receptor expression and IL-2 production. This cytokine also acts synergistically with other proteins to affect haematopoiesis, macrophage and osteoclast differentiation and platelet production. IL-6 is an interleukin that acts as both, a pro-inflammatory and an anti-inflammatory cytokine. In acute inflammation it acts as anti-inflammatory while in chronic inflammatory conditions such as collagen-induced arthritis or murine colitis, IL-6 is pro-inflammatory (Arthritis Research and Therapy, 2006, 8 (Suppl 2):S3).

IL-6 has been implicated as a mediator in inflammatory disorders, multiple myelomas, plasmacytomas, Castleman's disease, polyclonal B-cell activation and autoimmune diseases. It is secreted by T cells and macrophages to stimulate immune response to trauma, especially burns or other tissue damage leading to inflammation. It is significantly elevated with exercise, and precedes the appearance of other cytokines in the circulation. Inhibitors of IL-6 are used to treat postmenopausal osteoporosis. IL-6 is also relevant to many diseases such as diabetes, atherosclerosis, depression, systemic lupus erythematosus, prostate cancer, and rheumatoid arthritis. Advanced/metastatic cancer patients have higher levels of IL-6 in their blood.

The first line of treatment for inflammatory disorders involves the use of non-steroidal anti-inflammatory drugs (NSAIDs) e.g. ibuprofen, naproxen to alleviate symptoms such as pain. However, despite the widespread use of NSAIDs, many individuals cannot tolerate the doses necessary to treat the disorder over a prolonged period of time as NSAIDs are known to cause gastric erosions. Moreover, NSAIDs merely treat the symptoms of disorder and not the cause. When patients fail to respond to NSAIDs, other drugs such as methotrexate, gold salts, D-penicillamine and corticosteroids are used. These drugs also have significant toxic effects.

Monoclonal antibody drugs such as Infliximab, Etanercept and Adalimumab are useful as anti-inflammatory agents, but have drawbacks such as route of administration (only parenteral), high cost and activation of latent tuberculosis. (Rheumatology, 2007, 46(5): 887-888, Clin. Infect. Dis., 39: 295-299 and Ann. Rheum. Dis., 64 (Suppl III): 86).

Despite the available treatment options for the treatment of inflammatory disorders, there still exists a need for improved and alternative medicaments for the treatment of inflammatory disorders.

SUMMARY OF THE INVENTION

The present invention relates to novel compounds of formula I and formula II (as described herein) obtained by fermentation of Myxobacteria strain, referred to as culture no. PM0670013 (MTCC 5570).

The present invention also relates to purified compounds of formula I and formula II, isolated from the fermented broth of the culture no. PM0670013 (MTCC 5570), having anti-inflammatory activity.

The present invention also relates to compounds of formula I and formula II, and stereoisomers thereof, useful for the treatment of inflammatory disorders mediated by Interleukin-6 (IL-6).

The present invention also relates to compounds of formula I and formula II, and stereoisomers thereof, useful for the treatment of inflammatory disorders mediated by TNF-α.

The invention further relates to a pharmaceutical composition comprising a compound of formula I or a compound of formula II or a stereoisomer thereof in association with a pharmaceutically acceptable carrier, adjuvant or vehicle for the treatment of inflammatory disorders.

The present invention also relates to processes for the isolation of a culture no. PM0670013 (MTCC 5570), which on cultivation produces the compounds of formula I and formula II.

The present invention further relates to processes for the production of the compound of formula I and the compound of formula II or stereoisomers thereof from the culture no. PM0670013 (MTCC 5570) or mutants or variants thereof.

BRIEF DESCRIPTION OF THE DRAWINGS

Preferred features of the invention can be understood from a review of the following detailed description and drawings, wherein:

FIG. 1 illustrates $^1$H NMR (500 MHz, CDCl$_3$; Instrument: Bruker) of the compound of formula I.

FIG. 2 illustrates $^1$H NMR (500 MHz, CDCl$_3$; Instrument: Bruker) of the compound of formula II.

DETAILED DESCRIPTION OF THE INVENTION

The compound of formula I has the molecular formula C$_{13}$H$_{21}$NO$_4$ (molecular weight 255.15) and the compound of formula II has the molecular formula C$_{13}$H$_{28}$N$_2$O$_2$ (molecular weight 244.36). The compounds may be characterized by any one or more of its physico-chemical and spectral properties, such as high performance liquid chromatography (HPLC), high resolution mass spectrum (FIRMS), infra red (IR) and nuclear magnetic resonance (NMR) spectroscopic data as discussed herein below.

The structures of the formula I and formula II have been elucidated.

The compounds of formula I and formula II are structurally represented below:

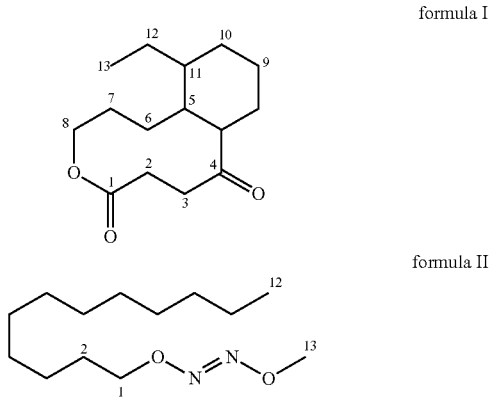

formula I formula II

The compounds of formula I and formula II have anti-inflammatory activity.

The microorganism, which may be used for the production of the above compounds is a strain of Myxobacteria (PM0670013/MTCC 5570), herein after referred to as culture no. PM0670013, isolated from a soil sample collected from paddy crop field from Langaneshwar, Orissa, India.

The present invention further provides processes for the production of the compound of formula I and formula II from culture no. PM0670013, comprising the steps of: (a) cultivating the culture no. PM0670013 (MTCC 5570) or one of its variants or mutants under submerged aerobic conditions in a nutrient medium containing one or more sources of carbon and one or more sources of nitrogen and optionally nutrient inorganic salts to produce the compounds of formula I and the compound of formula II;

(b) isolating the compounds of formula I and formula II from the culture broth or fermentated broth; and (c) purifying the compounds of formula I and formula II.

The step (c) involving purification of the compounds of formula I and formula II using is carried out by purification procedures generally used in the related art.

The compound of formula I and the compound of formula II produced according to the process of the present invention are substantially pure compounds.

The term "mutant" as used herein, refers to an organism or cell carrying a mutation, which is an alternative phenotype to the wild-type.

The term "variant" as used herein, refers to an individual organism that is recognizably different from an arbitrary standard type in that species.

The term "Myxobacteria" as used herein, refers to a group of gram negative cubacteria, belonging to the delta group of the proteobacteria.

The term "mammal" as used herein, refers to a human as well as non-human mammal, including but not limited to, cows, horses, pigs, dogs and cats. The term "mammal" may be used interchangeably with the term "patient".

The term "whole broth" may be used interchangeably with the terms "nutrient broth", culture broth or "fermented broth".

The term "nutrient medium" as used herein, refers to a medium that is suitable for cultivation of culture no. PM0670013. In general, a nutrient medium comprises a carbon source, a nitrogen source, trace elements such as inorganic salts, optionally vitamins or other growth factors and water. The term "nutrient medium" encompasses isolation medium, culture medium, production medium, seed medium, maintenance medium and purification medium.

The term "active ingredient" as used herein, refers to the compound of formula I or to the compound of formula II or to a stereoisomer thereof.

The term "substantially pure" as used herein, means that the compound of formula I and compound of formula II and stereoisomers thereof are sufficiently pure such that further purification would not detectably alter the physical and chemical properties, such as enzymatic and biological activities, of the substance. Compounds of formula I and II can be purified substantially by following the methods known to those skilled in the art.

A substantially chemically pure compound can, however, be a mixture of stereoisomers. In such instances, further purification may increase the anti-inflammatory activity of the compound.

Preliminary identification of culture no. PM0670013 (source of compounds of formula I and formula II) as Myxobacteria was done on the basis of its colony morphology, wet mount tests and Gram stain reaction.

Culture no. PM0670013 can be isolated on modified salt solution of Mandels containing 15 g/l, agar. The soil sample on incubation at 28-32° C. for about 3-5 weeks on modified salt solution of Mandels developed a stout translucent and shining stalk with almost spherical orange colored shiny head. Wet mount of the culture under phase contrast light microscopy showed short, sluggishly motile coccobacilli at 400× magnification. Gram stain revealed grain-negative bacilli. Thus, culture no. PM0670013 was identified as a strain of Myxobacteria.

Culture no. PM0670013 has been deposited with Microbial Type Culture Collection (MTCC), Institute of Microbial Technology, Sector 39-A, Chandigarh-160 036, India, a World Intellectual Property Organization (WIPO) recognized International Depository Authority (IDA) on Aug. 30, 2010 and has been given the accession number MTCC 5570.

In addition to the specific microorganism described herein, it should be understood that mutants, such as those produced by the use of chemical or physical mutagens including X-rays, U.V. rays etc. and organisms whose genetic makeup has been modified by molecular biology techniques, may also be cultivated to produce the compounds of formula I and formula II.

Suitable mutants and variants of culture no. PM0670013 can be identified by confirming the production of the compounds of the present invention by HPLC and/or determination of biological activity of the active compounds accumulated in the culture broth, for example by testing the compounds for anti-inflammatory activity by the method as described herein.

The medium and/or nutrient medium used for isolation and cultivation of culture no. PM0670013, which produces the compounds of formula I and formula II, preferably contains sources of carbon, nitrogen and nutrient inorganic salts. The carbon sources are, for example, one or more of cellulose, soluble starch, glucose, sucrose, dextrin, fructose, dextrose, molasses, glycerol, lactose, or galactose. Preferred carbon sources are cellulose, soluble starch and glucose. The sources of nitrogen are, for example, one or more of soybean meal, papaic digest of soyabean meal, peanut meal, yeast extract, beef extract, peptone, casein peptone, pancreatic digest of casein, malt extract, corn steep liquor, gelatin, urea or casamino acids. Preferred nitrogen sources are casein peptone, peptone and soybean meal. The nutrient inorganic salts are, for example, one or more of sodium chloride, potassium chloride, calcium chloride, calcium chloride dihydrate, magnesium chloride, ferric chloride, strontium chloride, cobalt chloride, zinc chloride, potassium bromide, sodium fluoride, sodium hydrogen phosphate, potassium hydrogen phosphate, potassium dihydrogen phosphate, dipotassium hydrogen phosphate, magnesium phosphate, calcium carbonate, sodium bicarbonate, sodium silicate, ammonium nitrate, potassium nitrate, ferrous sulfate, sodium sulfate, ammonium sulfate, magnesium sulfate, magnesium sulfate heptahydrate, manganese sulfate, ferric citrate, boric acid or trace salt solution. Calcium chloride and magnesium sulfate are preferred salts.

The maintenance of culture no. PM0670013 may be carried out at a temperature ranging from 25° C. to 36° C. and a pH of about 5 to 8.5. Typically, culture no. PM0670013 is maintained at 28° C. to 32° C. and a pH of about 7.0 to 7.4. The well-grown cultures may be preserved in the refrigerator at 2° C. to 8° C.

Seed culture cultivation of culture no. PM0670013 may be carried out at a temperature ranging from 25° C. to 36° C. and a pH of about 5 to 8.5 for 24 hours to 96 hours at 220 rpm (revolutions per minute) to 260 rpm. Typically, culture no. PM0670013 seed is cultivated at 28° C. to 32° C. and a pH of about 6.5 to 7.5, for 46 hours to 50 hours at 240 rpm.

The production of the compounds of formula I and formula II may be carried out by cultivating culture no PM0670013 by fermentation at a temperature ranging from 28° C. to 34° C. and a pH of about 5 to 8.5, for 5 days to about 9 days at 220 rpm to 260 rpm. Typically, culture no. PM0670013 is cultivated at 28° C. to 32° C. and pH of about 6.5 to 7.5 for about 7 days.

The production of the compounds of formula I and formula II may be carried out by cultivating culture no PM0670013 by fermentation in a fermenter at a temperature ranging from 28° C. to 32° C., agitation ranging from 190-210 rpm, aeration ranging from 5-20 1 pm, and pH of about 6.5 to 7.5 for about 7 days.

The production of the compounds of formula I and formula II can be carried out by cultivating culture no. PM0670013 in a suitable nutrient broth under conditions described herein, preferably under submerged aerobic conditions, for example in shake flasks, as well as in laboratory fermenters. The progress of fermentation and production of the compounds of the present invention can be detected by, high performance liquid chromatography (HPLC) and by measuring the anti-inflammatory activity of the culture broth against IL-6 and TNF-α.

Resins such as XAD series of polymers (Rohm and Haas Industries, USA) can be used in fermentation media to adsorb the active molecules on their surfaces and later eluted using solvents such as methanol, acetone, acetonitrile, n-propanol, or iso-propanol or using a water immiscible solvent such as petroleum ether, dichloromethane, chloroform, ethyl acetate or butanol. Typically, the compounds of formula I and formula II are eluted using methanol. The eluates can be concentrated to obtain the crude material. Further, the crude material can be tested for biological activity.

The whole broth can be centrifuged to obtain cell mass and the culture filtrate.

Alternatively the whole broth, wherein XAD resins are not used in the fermentation can be centrifuged to obtain cell mass and the culture filtrate.

The compounds of formula I and formula II can be recovered from the cell mass by extraction with one or more water miscible solvents such as methanol, acetone, acetonitrile, n-propanol, or iso-propanol or with a water immiscible solvent such as petroleum ether, dichloromethane, chloroform, ethyl acetate or butanol. Typically, the compounds of formula I and formula II are extracted with methanol. Concentrates of these eluates can be tested for biological activity.

The compounds of formula I and formula II can be recovered from the culture filtrate by extraction with a water immiscible solvent such as petroleum ether, dichloromethane, chloroform, ethyl acetate, diethyl ether or butanol, or by hydrophobic interaction chromatography using polymeric resins such as "Diaion HP-20®" (Mitsubishi Chemical Industries Limited, Japan), "Amberlite XAD®" (Rohm and Haas Industries, USA) or adsorption on activated charcoal, which are eluted using water miscible solvent such as methanol, acetone, acetonitrile, n-propanol, or iso-propanol. Concentrates of these eluates can be tested for biological activity. These techniques may be used repeatedly.

The compounds of formula I and formula II of the present invention can be recovered from the crude material by fractionation using any of the following techniques: normal phase chromatography such as normal phase HPLC (using silica gel as stationary phase; eluents such as hexane, petroleum ether, ethyl acetate, dichloromethane, acetone, chloroform, methanol, or combinations thereof); reverse phase chromatography using reverse phase silica gel such as dimethyloctadecylsilyl silica gel, (RP-18) or dimethyloctylsilyl silica gel (RP-8) as stationary phase; and eluents such as water, buffers [for example, phosphate, acetate, citrate (pH 2 to 8)], and organic solvents (for example, methanol, acetonitrile, acetone, tetrahydrofuran, or combinations of these solvents); gel permeation chromatography (using resins such as Sephadex LH-20® (Pharmacia Chemical Industries, Sweden), TSK-gel® Toyopearl HW (TosoHaas, Tosoh Corporation, Japan) and eluents such as methanol, chloroform, acetone, ethyl acetate, or their combinations); or Sephadex® G-10 and G-25 in water); or by counter-current chromatography (using a biphasic eluent system made up of two or more solvents such as water, methanol, ethanol, iso-propanol, n-propanol, tetrahydrofuran, acetone, acetonitrile, methylene chloride, chloroform, ethyl acetate, petroleum ether, benzene, and toluene). These techniques may be used repeatedly, alone or in combination. A typical method is normal phase HPLC.

The compounds of present invention are inhibitors of IL-6 and TNF-α. Hence they can be used in the treatment of inflammatory disorders mediated by IL-6 and/or TNF-α such as, inflammatory bowel disease, inflammation, rheumatoid arthritis, juvenile rheumatoid arthritis, psoriatic arthritis, osteoarthritis, refractory rheumatoid arthritis, chronic non-rheumatoid arthritis, osteoporosis/bone resorption, Crohn's disease, septic shock, endotoxic shock, atherosclerosis, ischemia-reperfusion injury, coronary heart disease, vasculitis, amyloidosis, multiple sclerosis, sepsis, chronic recurrent uveitis, hepatitis C virus infection, malaria, ulcerative colitis, cachexia, psoriasis, plasmocytoma, endometriosis, Behcet's disease, Wegenrer's granulomatosis, autoimmune disease, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, meningitis, ankylosing spondylitis, skin delayed type hypersensitivity disorders, Alzheimer's disease, systemic lupus erythematosus and allergic asthma.

According to another aspect of the present invention, there is provided a method for the treatment of inflammatory disorders mediated by IL-6 or TNF-α, comprising administering to a mammal in need thereof a therapeutically effective amount of a compound of formula I or a compound of formula II or a stereoisomer thereof.

According to another aspect of the present invention, there is provided a method for the treatment of inflammatory disorders mediated by IL-6 or TNF-α selected from inflammatory bowel disease, rheumatoid arthritis, juvenile rheumatoid arthritis, psoriatic arthritis, osteoarthritis, psoriasis and ulcerative colitis, comprising administering to a mammal in need thereof a therapeutically effective amount of a compound of formula I or a compound of formula II or a stereoisomer thereof.

According to another aspect of the present invention, there is provided a method for the treatment of inflammatory disorders mediated by IL-6 selected from rheumatoid arthritis, osteoarthritis and other autoimmune conditions such as ankylosing spondylitis, Crohn's disease and psoriasis, comprising administering to a mammal in need thereof a therapeutically effective amount of a compound of formula I or a compound of formula II or a stereoisomer thereof.

According to another aspect of the present invention, there is provided the use of a compound of formula I or a compound of formula II or a stereoisomer thereof for the manufacture of a medicament for the treatment of inflammatory disorders mediated by IL-6 or TNF-α.

According to another aspect of the present invention, there is provided the use of a compound of formula I or compound of formula II or a stereoisomer thereof for the manufacture of a medicament for the treatment of inflammatory disorders mediated by IL-6 or TNF-α selected from inflammatory bowel disease, rheumatoid arthritis, juvenile rheumatoid arthritis, psoriatic arthritis, osteoarthritis, psoriasis and ulcerative colitis.

According to another aspect of the present invention, there is provided the use of a compound of formula I or of the compound of formula II or a stereoisomer thereof for the manufacture of a medicament for the treatment of inflammatory disorders mediated by IL-6 selected from rheumatoid arthritis, osteoarthritis and other autoimmune conditions.

The present invention further relates to pharmaceutical compositions, which contain an effective amount of a compound of formula I or a compound of formula II or a stereoisomer thereof, together with a pharmaceutically acceptable carrier. The effective amount of an active ingredient in the pharmaceutical preparations normally is from about 0.01 mg to 1000 mg.

According to another embodiment of the present invention there is provided a pharmaceutical composition comprising a compound of formula I or a compound of formula II or a stereoisomer thereof, in association with a pharmaceutically acceptable carrier or excipient for the treatment of inflammatory disorders mediated by IL-6 or TNF-α.

The compounds of the present invention can be administered orally, nasally, topically, subcutaneously, intramuscularly, intravenously, rectally or by other modes of administration.

Pharmaceutical compositions which contain compound of formula I or a compound of formula II or a stereoisomer thereof, optionally with other pharmaceutically active substances such as non-steroidal anti-inflammatory agents for example, sodium cromoglycate, nedocromil sodium, Ketotifen; steroidal anti-inflammatory agent, for example, corticosteroid; a $\beta_2$ adrenergic receptor agonist or a phosphodiesterase-4 inhibitor; and the like; can be prepared by mixing the active compounds with one or more pharmacologically tolerated auxiliaries and/or excipients such as, wetting agents, solubilisers such as surfactants, vehicles, tonicity agents, fillers, colorants, masking flavors, lubricants, disintegrants, diluents such as water, binders, plasticizers, emulsifiers, ointment bases, emollients, thickening agents, polymers, lipids, oils, cosolvents, complexation agents, or buffer substances, and converting the mixture into a suitable pharmaceutical form such as, for example, tablets, coated tablets, capsules, suppositories, granules, powders, creams, ointments, gels, syrup, emulsions, suspensions or solutions suitable for parenteral administration.

Examples of auxiliaries and/or excipients that may be mentioned are surfactants such as cremophor, poloxamer, benzalkonium chloride and sodium lauryl sulfate; moisturizing agent such as glycerin and starch; glidants such as magnesium stearate, polyethylene glycol and talc; fillers such as lactose, mannitol, dextrose, sorbitol and sucrose; binders such as lactose, dibasic calcium phosphate, sucrose, corn starch, microcrystalline cellulose and modified cellulose for example hydroxypropyl methylcellulose.

The dose of the compounds of this invention, which is to be administered, can cover a wide range. A suitable dosage is about 0.1 mg to 50 mg/kg/day of the compound of formula I or II and/or a stereoisomer, for example, about 1 to 20 mg/kg/day. If required, higher or lower daily doses can also be administered. Actual dosage levels of the active ingredients in the pharmaceutical compositions of this invention may be varied so as to obtain an amount of the active ingredient, which is effective to achieve the desired therapeutic response for a particular patient, composition, and mode of administration without being toxic or resulting in unacceptable side effects to the patient.

The following are provided as illustrative examples of the present invention and do not limit the scope thereof.

EXAMPLES

Unless otherwise stated all temperatures are in degree Celsius. Also, in these examples and elsewhere, abbreviations have the following meanings:

| List of abbreviations | |
|---|---|
| $CO_2$ | Carbon dioxide |
| DMSO | Dimethylsulfoxide |
| EDTA | Ethylene Diamine Tetra Acetic acid |
| ELISA | Enzyme-Linked Immunosorbent Assay |

-continued

| | List of abbreviations |
|---|---|
| g | Gram |
| HPLC | High Performance Liquid Chromatography |
| µg | Microgram |
| µ | Micron |
| mm | Millimeter |
| MEM | Minimal Essential Medium |
| nm | Nanometer |
| L | Liter |
| LPS | Lipopolysaccharide |
| lpm | Liter per minute |
| mg | Milligram |
| mL | Milliliter |
| min | Minutes |
| µl | Microliter |
| U/mL | Units/milliliter |
| rpm | Revolutions per minute |
| $R_t$ | Retention time |
| RT | Room Temperature 25 ± 5° C. |

Example 1

Isolation of Culture No. PM0670013 a) Composition of the Medium (Modified Salt Solution of Mandels)

Ammonium sulfate 1.4 g, urea 0.3 g, potassium hydrogen phosphate 2.0 g, calcium chloride 0.3 g, magnesium chloride 0.3 g, ferrous sulfate 0.005 g, cobalt chloride 0.008 g, manganese sulfate 0.016 g, zinc chloride 0.014 g, cellulose filter paper disc, agar 15 g, distilled water to make up the final volume of 1 L and pH was adjusted to 7. Amphotericin B (50 µg/mL) was added to the isolation medium to suppress the growth of yeast and fungi.

b) Procedure

Collection: Soil sample of about 2 g was collected from deep roots of paddy crop at Langaneshwar, Orissa. India and the sample was preserved at 2-8° C. before use for isolation of Myxobacteria.

Isolation: The filter paper disc was placed firmly on the isolation medium (agarified plates of modified salt solution of Mandels). The soil sample (~1 mg) was streaked on filter paper or placed in the form of four patches. The plates were incubated at about 30° C. till colonies were observed. Light orange colored colonies at the end of the filter paper appeared after about 4 weeks. These colonies were isolated and grown again on a fresh isolation medium and incubated further for 30 days to obtain pure culture. The culture revealed a stout translucent and shining stalk with spherical orange colored shiny head. Considering this morphology it was categorized under the genus *Myxococcus*.

Example 2

Purification of Culture No. PM0670013 a) Composition of the Purification Medium (Minimal Medium g/L)

Glucose 0.5 g, peptone 0.5 g, magnesium sulfate 0.1 g, calcium carbonate 0.1 g, agar powder 20 g, distilled water to make up the final volume of 1 L and pH was adjusted to 7.

b) Procedure

Metronidazole (20 µg/mL) was added to the culture to obtain protozoa free culture. A single fruiting body of Myxobacteria was then transferred to fresh minimal medium and allowed to grow. The procedure was repeated till pure culture was obtained. The purified isolate was given culture ID as PM0670013.

Example 3

Maintenance of Culture No. PM0670013 a) Composition of Medium (Soybean Casein Digest Agar Plates g/L, Hi Media)

Pancreatic digest of casein 17 g, Papaic digest of soyabean meal 3 g, Sodium chloride 5 g, dipotassium hydrogen phosphate 2.5 g, dextrose 2.5 g, agar 16 g, distilled water to make up the final volume 1 L and pH (at 25° C.) was adjusted to 7.

b) Procedure

The maintenance medium (Soybean casein digest agar) was prepared and distributed in test tubes. It was then sterilized at 121° C. for 30 minutes. The test tubes were cooled and allowed to solidify in a slanting position. The agar slants were streaked with pure culture of PM0670013. The plates were incubated at about 30° C. overnight for good growth of the culture. The well-grown cultures were stored in the refrigerator at 2° C. to 8° C.

Example 4

Fermentation of the Culture No. PM0670013 in Shake Flasks a) Composition of Seed Medium Starch 8 g, glucose 2 g, magnesium sulfate. $7H_2O$ 1 g, calcium chloride 1 g, EDTA 0.0008 g, peptone 4 g and distilled water to make up the final volume 1 L, pH was adjusted to 7.2.

b) The above medium was distributed in 100 mL amounts in 500 mL capacity Erlenmeyer flasks and sterilized at 121° C. for about 15 minutes. The flasks were cooled to RT and each flask was inoculated with well-grown producing strain (culture no. PM0670013) and the flasks were fermented on rotary shaker for 48 hours at 240 rpm at 30° C. to give seed culture.

c) Composition of the Production Medium

Soluble starch 5 g, casein peptone 2.5 g, magnesium sulfate. $7H_2O$ 0.5 g, dipotassium hydrogen phosphate 0.25 g, and distilled water to make up the final volume 1 L and pH was adjusted to about 7.

d) 100 mL of the production media in 500 mL capacity conical flasks together with 1% XAD 1180N resin (Rohm and Haas Industries, USA) was sterilized at 121° C. for 15 minutes, cooled to RT and then seeded with 2.5% (v/v) seed culture of step b and subjected to fermentation.

e) Fermentation Parameters

Temperature 30° C.; agitation 240 rpm and harvest time 7 days f) Preparation of the Crude Material The production flasks were harvested and the resin was separated from the whole broth by filtration. The resin was washed with de-mineralized water. The resin free broth was centrifuged at about 10,000 rpm for about 30 min. The supernatant was decanted and the remnant cell mass was obtained. The compounds of the present invention were recovered from the cell mass by extracting with methanol (fraction 1). The compounds adsorbed on the resin were eluted with methanol (fraction 2). Methanol extracts of fractions 1 and 2 were concentrated separately and dried to obtain the crude material.

Example 5

Cultivation of the Culture No PM0670013 in Fermenter

Preparation of Seed Culture a) Composition of seed medium: Soluble starch 8 g, glucose 2 g, magnesium sulfate heptahydrate 1 g, calcium chloride dihydrate 1 g, EDTA 0.008 g, peptone 4 g, demineralized water to make up the final volume 1 L, pH was adjusted to 6.5-7.5 before sterilization.

b) The above medium was distributed in 200 ml aliquots in 1000 ml Erlenmeyer flasks and autoclaved at 121° C. for 30 min. The flasks were cooled to RT and each flask was inoculated with a loopful of the well-grown producing strain (PM0670013) from a culture slope and shaken on a rotary shaker for 46-48 hours at 230-250 rpm at 29-30° C. to give seed culture.

Production in Fermenter a) Composition of production medium: Soluble starch 5 g, casein peptone 2.5 g, magnesium sulfate heptahydrate 0.5 g, di potassium hydrogen phosphate 0.25 g, demineralized water to make up the final volume of 1 L and pH was adjusted to 6.5-7.5 before sterilization.

b) 20 L of the production medium in 25 L fermenter along with 800 μL, of desmophen as an antifoaming agent was sterilized in situ for 30 min at 121° C., cooled to 29-30° C. and seeded with 600 mL of the seed culture mentioned above.

c) Fermentation parameters: The fermentation was carried out at a temperature of 29-30° C., agitation 200 rpm, aeration 10 1 pm, and was harvested at 166 hours to 168 hours. The harvest pH of the culture broth was 6.5-7.5. The culture broth on harvest was used for isolation and purification of the compounds of the present invention.

d) Preparation of the crude material: The whole broth (18 L) was harvested and extracted using methanol (1.8 L) by stirring and followed by ethyl acetate (16.2 L). The organic layer was separated using disc stack separator (Alfa laval, model no LAPX404) and concentrated to obtain the crude material.

Example 6

Bioassay Guided Isolation and Characterization of Compounds of Formula I and Formula II The crude material of Example 5 (20 mg) was subjected to normal phase analytical HPLC separation.

Analytical HPLC Conditions:

| Column | silica (5μ, 4.6 × 250 mm) |
|---|---|
| Eluent | dichloromethane:methanol (90:10) |
| Flow rate | 1 mL/minute |
| Sample | 10 mg/mL in methanol |
| Injection volume | 10 μl |
| Run time | 20 min |
| Detection (UV) | 254 nm |
| Column temperature | 40° C. |

The chromatogram displayed five major peaks A ($R_t$=3.199), B ($R_t$=3.439), C ($R_t$=3.980), D ($R_t$=5.605) and E ($R_t$=6.464) and two minor peaks CO ($R_1$=4.456) and C210 ($R_t$=4.649). The compound of formula I eluted between 6 to 7 minutes and the compound of formula II eluted between 5 to 6 minutes.

The crude material of Example 5 (8.56 g) from 20 L batch was subjected to preparative HPLC separation, based on the profile as obtained in the analytical HPLC.

Preparative HPLC Conditions:

| Column | silica (10μ, 21.5 × 250 mm) |
|---|---|
| Eluent | dichloromethane:methanol (90:10) |
| Flow rate | 15 mL/minute |
| Sample | 80 mg/mL in methanol |
| Injection volume | 1.5 mL |
| Run time | 20 min |
| Detection (UV) | 254 nm |
| Column temperature | Room temperature |

The compound of formula I eluted between 11 to 12 minutes and the compound of formula II eluted between 10 to 11 minutes. The fractions collected were evaporated to dryness under reduced pressure.

The yield obtained was 1400, 1000, 96, 85, 63, 114 and 139 mgs for peaks A, B, C, CO, C210, D and E respectively. All fractions were tested for activity against IL-6 and INF-α by a method as described in Example 7. Peaks E and D exhibited IL-6 and TNF-α inhibition. Peak E (designated as compound of formula I) and D (designated as compound of formula II) were obtained in pure form for which structures were elucidated by studying physico-chemical properties.

Physical & Spectral Properties of the Compound of Formula I:

| | |
|---|---|
| Appearance | Off white solid |
| Solubility | Soluble in water, methanol, acetonitrile, chloroform and dichloromethane. |
| Molecular formula | $C_{13}H_{21}NO_4$ |
| Molecular weight | 255.15 |
| Mass | HR-ESI: 256.3015 [M + H]$^+$ |
| $^1$H NMR (500 MHz, CDCl$_3$) | refer to Table 1 and FIG. 1 |
| $^{13}$C NMR (75 MHz, CDCl$_3$) | refer to Table 1 |
| IR (KBr, cm$^{-1}$) | 2924, 2853, 1735, 1670, 1466, 1375 |
| UV | Detected by HPLC: UV spectrum recorded characteristic maxima at 228 and 258 nm |

TABLE 1

$^1$H NMR and $^{13}$C NMR of the compound of formula I

| Carbon Atom No. | Proton Chemical shifts $\delta_H$ (m, J (Hz)) | Carbon chemical shifts $\delta_C$ |
|---|---|---|
| 1 | NA | 168.8 |
| 2 | 2.62 (t, 8.0) | 32.27 |
| 3 | 2.82 (t, 8.0) | 26.55 |
| 4 | NA | 168.80 |
| 5 | 3.46 (m) | 54.00 |
| 6 | 1.35 (m) | 26.00 |
| 7 | 1.64 (t, 6.5) | 28.50 |
| 8 | 4.1 (t, 6.5) | 64.80 |
| 9 | 3.5 (m) | 67.43 |
| 10 | 1.75 (m) | 23.20 |
| 11 | 1.4 (m) | 29.60 |
| 12 | 1.31 (m) | 23.04 |
| 13 | 0.9 (t, 6.5) | 14.01 |

Physical & Spectral Properties of the Compound of Formula II:

| | |
|---|---|
| Appearance | Off white solid |
| Solubility | Soluble in water, methanol, acetonitrile, chloroform and dichloromethane. |
| Molecular formula | $C_{13}H_{28}N_2O_2$ |
| Molecular weight | 244.36 |
| Mass | ESI LCMS (+ve ion): 245.1 ($[M + H]^+$) |
| | ESI HRMS: 267.0787 $[M + Na]^+$ |
| $^1$H NMR (500 MHz, CDCl$_3$) | refer to Table 2 and FIG. 2 |
| $^{13}$C NMR (75 MHz, CDCl$^3$) | refer to Table 2 |
| IR (KBr, cm$^{-1}$) | 3378, 3016, 2918, 2850, 1663, 1463, 1235, 950, 729 |
| UV (nm) | Detected by HPLC: UV spectrum showed characteristic maxima at 229 and 264 |

TABLE 2

$^1$H NMR and $^{13}$C NMR of the compound of formula II

| Atom No. | Proton Chemical shifts $\delta_H$ (m, J (Hz)) | Carbon chemical shifts $\delta_C$ |
|---|---|---|
| 1 | 3.54 (t, 8.5) | 67.07 |
| 2 | 1.75 (m) | 23.2 |
| 3 | 1.39 (m) | 26.2 |
| 4 | 1.26 (s) | 29.67 |
| 5 | 1.26 (s) | 29.64 |
| 6 | 1.26 (s) | 29.58 |
| 7 | 1.26 (s) | 29.46 |
| 8 | 1.26 (s) | 29.36 |
| 9 | 1.29 (s) | 29.23 |
| 10 | 1.26 (s) | 31.90 |
| 11 | 1.29 (m) | 22.70 |
| 12 | 0.88 (t, 7.0) | 14.10 |
| 13 | 3.45 (s) | 53.40 |

Pharmacology

The efficacy of the compounds of formula I and formula II can be determined by a number of pharmacological assays well known in the art, such as described below. The exemplified pharmacological assays, which follow herein below, have been carried out with the compounds of the present invention.

In-Vitro Assays

Example 7

High Throughput Screening in LPS Stimulated THP-1 Cells

The assay was designed on the basis of the reference, The Journal of Immunology, 1993, 151 (10), 5631-5638, the disclosure of which is incorporated by reference for the teaching of the assay.

THP-1 (ATCC, USA) cells were cultured in RPMI 1640 (Roswell Park Memorial Institute) culture medium (Gibco BRL, Pasley, UK) containing 100 U/ml penicillin, 100 mg/mL streptomycin (100× solution, Sigma Chemical Co. St Louis, Mo., USA) and 10% fetal bovine serum (Gibco BRL, Pasley, UK). The cells were differentiated into macrophages with phorbol myristate acetate (Sigma, USA) in 96 well culture plates. Following cell plating, various concentrations of the compound of formula I or the compound of formula II or vehicle (0.5% DMSO) were added to each well and the plate was incubated for 30 min at 37° C. Finally, per well, 20 µL of LPS (10 µg/mL stock solution) (*Escherchia coli* 0127:B8, Sigma Chemical Co., St. Louis, Mo.) was added for a final concentration of 1 µg/mL. Plates were incubated at 37° C. for 24 hours in an atmosphere of 5% $CO_2$. Supernatants were harvested, and assayed for TNF-α and IL-6 by ELISA as described by the manufacturer (BD Biosciences). Percent inhibition of cytokine release compared to the control was calculated. The 50% inhibitory concentration ($IC_{50}$) values were calculated by a nonlinear regression method. The results are indicated in Table 3.

Dexamethasone was used as standard. Dexamethasone shows 73% inhibition and 84% inhibition of TNF-α and IL-6 respectively at 1 µg/ml.

TABLE 3

| Compound | $IC_{50}$ TNF-α (µg/ml) | $IC_{50}$ IL-6 (µg/ml) |
|---|---|---|
| Compound of formula I | 1.5 | 0.5 |
| Compound of formula II | 1.5 | 1.2 |

Example 8

Determination of Cytotoxicity of Compound of Formula I

Cytotoxicity assay (CCK-8) was used to study cytotoxicity of the compound of formula I. The MCF 10A (non-tumorigenic human mammary epithelial cell line, ATCC, USA) cell line was used.

The CCK-8 allows very convenient assays by utilizing Dojindo's highly water-soluble tetrazolium salt. CCK-8 solution (WST-8 [2-(2-methoxy-4-nitrophenyl)-3-(4-nitrophenyl)-5-(2,4-disulfophenyl)-2H-tetrazolium, monosodium salt]) produces a water-soluble formazan dye upon reduction in the presence of an electron mediator.

Cells were seeded at a density of $3 \times 10^3$ to $5 \times 10^3$ per well (in 0.09 ml volume) in transparent 96 well tissue culture plate (NUNC, USA) and allowed to incubate at 37° C. in 5% $CO_2$ incubator for 2-6 h. The compound of formula I was diluted in MEM medium at various concentrations and 0.01 ml of 10× stocks were added to each well in triplicate. Plates were incubated at 37° C. in 5% $CO_2$ incubator for 72 h, with an intermittent microscopic observation every 24 h. After 72 h incubation, 10 µA CCK-8 solution was added to each well, and plates were further incubated in same incubation conditions for 4 h, followed by spectrophotometeric absorbance at 450 nm on a plate reader. The $IC_{50}$ value of compound of formula I for cell toxicity against normal cell line, MCF 10A is depicted in Table 4.

TABLE 4

Cytotoxicity results of compound of formula I on MCF 10 A cell line

| | $IC_{50}$ (µg/mL) |
|---|---|
| Compound of formula I | 9.9 |

Conclusion: The compound of formula I was found to be non-cytotoxic

The invention claimed is:
1. A compound selected from the group consisting of the compound of formula I and the compound of formula II,

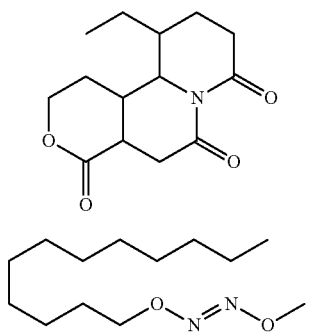

formula I

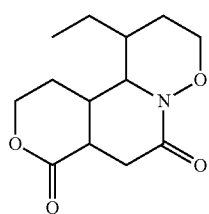

formula II or a stereoisomer thereof.

2. The compound according to claim 1 of formula I;

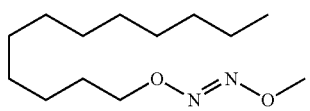

formula I or a stereoisomer thereof.

3. The compound of formula I, or a stereoisomer thereof, according to claim 2, wherein
   (a) molecular weight is 255.15,
   (b) molecular formula is $C_{13}H_{21}NO_4$,
   (c) $^1$H NMR spectrum (500 MHz, $CDCl_3$) is: δ 4.1 (t, 6.5 Hz, 2H), 3.5 (m, 2H), 3.46 (m, 1H), 2.82 (t, 8 Hz, 2H), 2.62 (t, 8 Hz, 2H), 1.75 (m, 2H), 1.64 (t, 6.5 Hz, 2H), 1.4 (m, 1H), 1.35 (m, 2H), 1.31 (m, 2H), 0.9 (t, 6.5 Hz, 3H) (as depicted in FIG. 1),
   (d) $^{13}$C NMR spectrum (75 MHz, $CDCl_3$) is: δ 168.8 (2C), 67.43, 64.80, 54.00, 32.27, 29.60, 28.50, 26.55, 26.00, 23.20, 23.04, 14.01, and
   (e) IR (KBr) spectrum is 2924, 2853, 1735, 1670, 1466, 1375 cm$^{-1}$.

4. The compound of Formula II according to claim 1;

formula II or a stereoisomer thereof.

5. The compound of formula II, or a stereoisomer thereof, according to claim 4, wherein
   (a) molecular weight is 244.36,
   (b) molecular formula is $C_{13}H_{28}N_2O_2$,
   (c) $^1$H NMR spectrum (500 MHz, $CDCl_3$) is: δ 3.54 (t, 8.5 Hz, 2H), 3.45 (s, 3H), 1.75 (m, 2H), 1.39 (m, 2H), 1.29 (s, 4H), 1.26 (s, 12H), 0.88 (t, 7 Hz, 3H) (as depicted in FIG. 2);
   (d) $^{13}$C NMR spectrum (75 MHz, $CDCl_3$) is: δ 67.07, 53.40, 31.90, 29.67, 29.64, 29.58, 29.46, 29.36, 29.23, 26.2, 23.2, 22.70, 14.10, and
   (e) IR (KBr) spectrum is 3378, 3016, 2918, 2850, 1663, 1463, 1235, 950, 729 cm$^{-1}$.

6. A process for the production of the compound of formula I and compound of formula II as defined in claim 1, comprising the steps of:
   (a) cultivating the culture no. PM0670013 (MTCC 5570) or one of its variants or mutants by fermentation, under submerged aerobic conditions in a nutrient medium containing sources of carbon, nitrogen and inorganic salts to produce the compound of formula I and compound of formula II,
   (b) isolating the compound of formula I and compound of formula II by extraction or fractionation using a solvent from the fermented broth, and
   (c) purifying the compound of formula I and the compound of formula II.

7. A pharmaceutical composition comprising a therapeutically effective amount of the compound of formula I or the compound of formula II according to claim 1 or a stereoisomer thereof; and a pharmaceutically acceptable carrier or diluent.

8. A method for the treatment of an inflammatory disorder mediated by tumor necrosis factor-α (TNF-α) or interleukin-6 (IL-6) or a combination thereof, comprising administering to a mammal in need thereof a therapeutically effective amount of the compound of formula I or the compound of formula II according to claim 1 or a stereoisomer thereof, wherein the inflammatory disorder mediated by TNF-α or IL-6 is selected from the group consisting of inflammatory bowel disease, inflammation, rheumatoid arthritis, juvenile rheumatoid arthritis, psoriatic arthritis, osteoarthritis, refractory rheumatoid arthritis, chronic non-rheumatoid arthritis, ulcerative colitis, Crohn's disease, ankylosing spondylitis, psoriasis and systemic lupus erythematosus.

\* \* \* \* \*

UNITED STATES PATENT AND TRADEMARK OFFICE
CERTIFICATE OF CORRECTION

PATENT NO. : 8,263,579 B2
APPLICATION NO. : 13/012463
DATED : September 11, 2012
INVENTOR(S) : Koteppa Pari et al.

It is certified that error appears in the above-identified patent and that said Letters Patent is hereby corrected as shown below:

In the Specification

Column 3, lines 21-30, replace 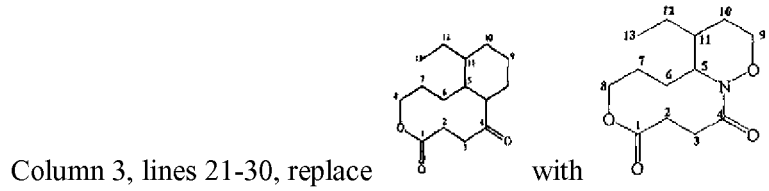 with

Signed and Sealed this
First Day of October, 2013

Teresa Stanek Rea
*Deputy Director of the United States Patent and Trademark Office*